(12) United States Patent
Kwoen

(10) Patent No.: US 7,259,681 B2
(45) Date of Patent: Aug. 21, 2007

(54) SYSTEM AND METHOD OF PERFORMING MEDICAL DIAGNOSIS IN REAL TIME

(75) Inventor: O Seong Kwoen, Seoul (KR)

(73) Assignee: LG Electronics Inc., Seoul (KR)

( * ) Notice: Subject to any disclaimer, the term of this patent is extended or adjusted under 35 U.S.C. 154(b) by 0 days.

(21) Appl. No.: 11/127,281

(22) Filed: May 12, 2005

(65) Prior Publication Data

US 2005/0208969 A1 Sep. 22, 2005

Related U.S. Application Data

(63) Continuation of application No. 10/118,232, filed on Apr. 9, 2002, now Pat. No. 6,903,657.

(30) Foreign Application Priority Data

Apr. 17, 2001 (KR) ............... 2001-20521

(51) Int. Cl.
*G08B 23/00* (2006.01)
(52) U.S. Cl. .............. 340/573.1; 340/573.3; 340/5.84; 340/825.57; 600/300; 600/306; 128/920; 128/923
(58) Field of Classification Search ............. 340/573.1, 340/573.3, 5.84, 825.57, 582, 5.81, 5.85, 340/5.86; 600/300, 306; 128/920, 923
See application file for complete search history.

(56) References Cited

U.S. PATENT DOCUMENTS

| 5,772,586 | A | 6/1998 | Heinonen et al. ........... 600/300 |
| 6,238,338 | B1* | 5/2001 | DeLuca et al. ............. 600/300 |
| 6,331,160 | B1* | 12/2001 | Bardy ........................ 600/300 |
| 6,334,778 | B1* | 1/2002 | Brown ........................ 434/258 |
| 6,366,871 | B1* | 4/2002 | Geva ........................... 702/188 |
| 6,396,416 | B1* | 5/2002 | Kuusela et al. ........ 340/870.28 |
| 6,497,655 | B1* | 12/2002 | Linberg et al. ............. 600/300 |
| 6,616,613 | B1 | 9/2003 | Goodman ................... 600/504 |
| 2002/0082665 | A1 | 6/2002 | Haller et al. .................. 607/60 |

* cited by examiner

*Primary Examiner*—Benjamin C. Lee
*Assistant Examiner*—Daniel Previl
(74) *Attorney, Agent, or Firm*—KED & Associates, LLP

(57) ABSTRACT

A system and method of performing a medical diagnosis in real time that can diagnose a health condition of a mobile terminal user in real time is disclosed. Various sensors provided in the mobile terminal sense a body condition, and a server diagnoses the health condition of the user from the sensed condition information, and informs the user of the corresponding health keeping plan and medical treatment as well. Thus, the user can conveniently check his/her health condition any time and anywhere.

28 Claims, 5 Drawing Sheets

SYSTEM AND METHOD OF PERFORMING MEDICAL DIAGNOSIS IN REAL TIME

CROSS-REFERENCE TO RELATED APPLICATIONS

This application is a CON of Ser. No. 10/118,232 Apr. 9, 2002, U.S. Pat. No. 6,903,657.

BACKGROUND OF THE INVENTION

1. Field of the Invention

The present invention relates to a system and method of performing a medical diagnosis in real time that can check a health condition of a user of a wireless mobile terminal in real time.

2. Discussion of the Related Art

With the rapid development of the communication technology, the use of Internet services and mobile communication services at home is continuously increasing.

In order to satisfy the increasing users' desires, various communication service providers provide diverse supplementary services.

In case of the Internet service, diverse works such as business, stock, game, search for information, etc., which have been performed through offline, are now being served online.

Also, in case of the mobile communication service, information desired by other parties can be transferred in the form of a voice, data, image, etc., irrespective of time and place.

Recently, a wireless Internet service wherein the Internet and the mobile communication network are connected together has been proposed. This wireless Internet service has been developed as a way to solve the drawbacks of the existing Internet services.

The existing Internet service instantly provides diverse information, but has drawbacks in that its mobility is not guaranteed with a limited locality in using the service. Also, the mobile communication service enables a phone call with its mobility assured, but has drawbacks in that it cannot provide diverse online service such as the Internet service.

Now, users of portable wireless terminals can receive diverse services of the existing Internet through the wireless Internet service currently provided.

However, the wireless Internet service also has limitations.

That is, the portable wireless terminal users can receive the Internet services such as a search for information, e-business, game, community, e-mail, etc., but it is almost impossible at present for the users to receive a service such as a remote medical service through the Internet. That is, though an interactive medical treatment is possible through a voice or pictorial call, it is very difficult to provide the service for receiving actual body information of a moving wireless terminal user and providing actual treatment information in real time.

SUMMARY OF THE INVENTION

Accordingly, the present invention is directed to a system and method of performing a medical diagnosis in real time that substantially obviates one or more problems due to limitations and disadvantages of the related art.

An object of the present invention is to provide a system and method of performing a medical diagnosis in real time that enables a health checkup of a mobile terminal user any time and anywhere through interworking between a server existing in a wireless network or Internet and a portable wireless terminal.

Another object of the present invention is to provide a system and method of performing a medical diagnosis in real time that can instantly informs a user of an actual health keeping plan and medical treatment based on actual body information of the user, and a change of his/her health condition.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, a system for performing a medical diagnosis in real time includes a detector for sensing a body condition, a mobile terminal for repeating sensed body condition information by wireless, and a server for analyzing the received body condition information, and informing a result of health checkup according to the analyzed body condition to the mobile terminal.

In another aspect of the present invention, a method of performing a medical diagnosis in real time in a wireless network system having a mobile terminal and a server, includes a first step of the mobile terminal sensing a body condition of a mobile terminal user, a second step of repeating a wireless signal including the sensed body condition information to the server, and a third step of the server examining a health condition by extracting the body condition information from the repeated wireless signal.

In still another aspect of the present invention, a method of performing a medical diagnosis in real time in a wireless network system having a mobile terminal and a server, includes a first step of detecting an electric response impedance value per body region of a mobile terminal user through sensors provided in the mobile terminal, a second step of the server diagnosing a nutritive condition, degree of fatness, and moisture distribution of the user from the detected impedance value per body region, and a third step of the server transferring a treatment according to the diagnosis to the mobile terminal.

In still another aspect of the present invention, a method of performing a medical diagnosis in real time in a wireless network system having a mobile terminal and a server, includes a first step of detecting a conductive response value of a mobile terminal user through sensors provided in the mobile terminal, and repeating the detected conductive response value by wireless, a second step of the server analyzing a psychology of the user from the conductive response value repeated by wireless, and a third step of the server transferring a treatment for improving the analyzed psychology to the mobile terminal.

In still another aspect of the present invention, a system for performing a medical diagnosis in real time includes sensors for sensing a conductive response value between specified body regions, a mobile terminal for repeating the sensed conductive response value by wireless, and a server for transmitting a wireless repeated signal received from the mobile terminal to another diagnosis terminal, and informing a result of health checkup and/or a corresponding treatment received from the diagnosis terminal to the mobile terminal.

In still another aspect of the present invention, a method of performing a medical diagnosis in real time in a wireless network system having a mobile terminal, a server, and a diagnosis terminal, includes a first step of the mobile terminal sensing a body condition of a mobile terminal user, a second step of repeating a wireless signal including the sensed body condition information to the server, a third step of the server transmitting the repeated wireless signal to the diagnosis terminal, a fourth step of the diagnosis terminal examining a health condition by extracting the body condition information from the repeated wireless signal, and a fifth step of transferring a result of health checkup and/or a corresponding treatment transmitted from the diagnosis terminal to the mobile terminal through the server.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
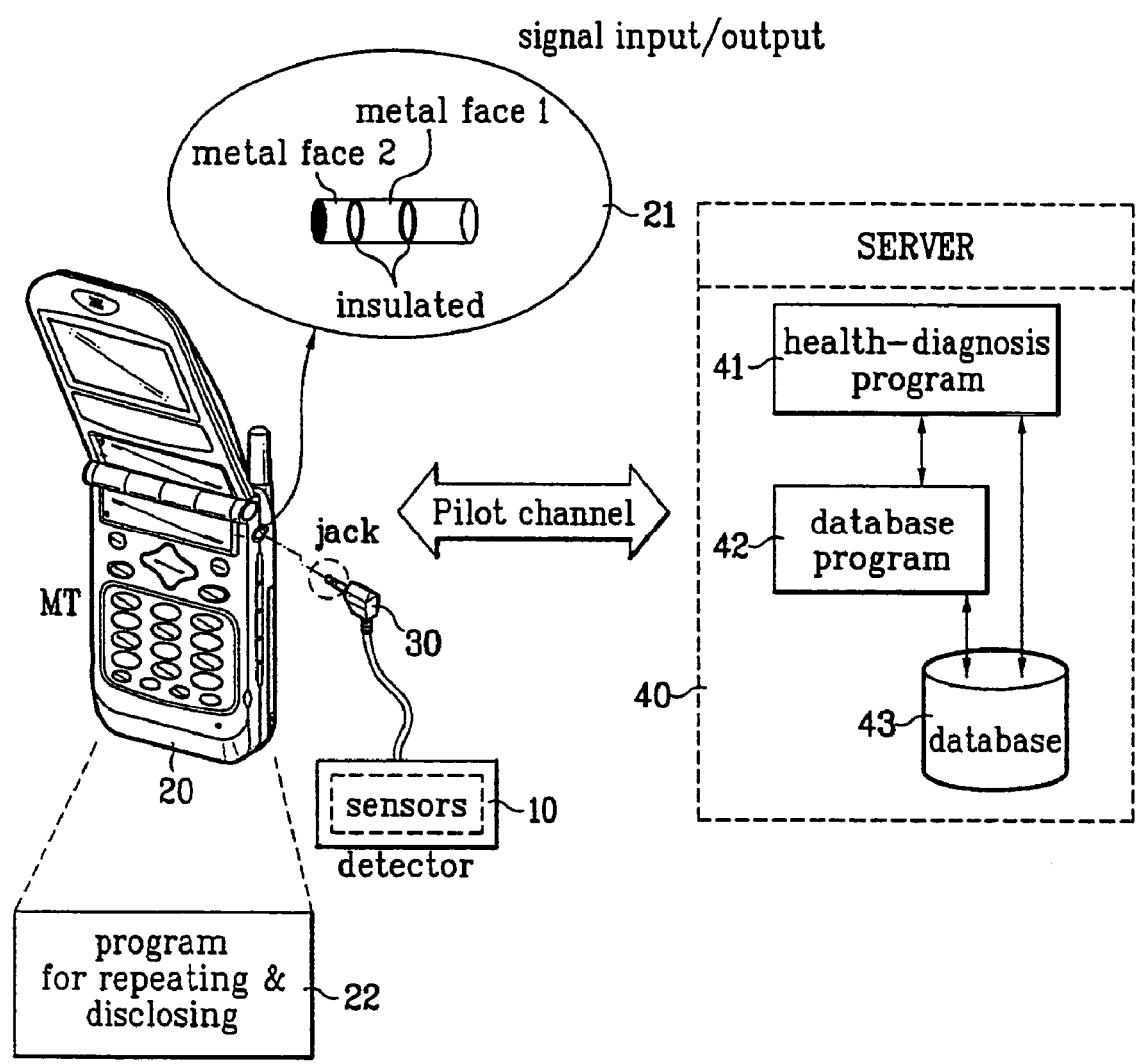
FIG. 1 is a view illustrating the construction of a system for performing a medical diagnosis in real time according to a first embodiment of the present invention.

FIG. 1 is a view illustrating the construction of a system for performing a medical diagnosis in real time according to a first embodiment of the present invention.

Referring to FIG. 1, the system for performing a medical diagnosis in real time according to the present invention includes a detector 10, a wireless mobile terminal (hereinafter referred to as MT) 20, and a server 20.

The detector 10 senses a body condition of a user of the MT 20.

The detector 10 has built-in sensors for detection of temperature/vibration/conductive response and brain waves to sense the body condition of the user. Specifically, the detector 10 has a built-in temperature sensor for sensing the body temperature of the user, a built-in vibration sensor for sensing the pulse of the user, or a built-in conductive response sensor for measuring a conductive response between specified regions of the user's body. For instance, as the conductive response sensor is used a galvanic skin response (GSR) sensor. Also, the detector 10 has a built-in electroencephalogram (EEG) sensor for detecting the brain waves of the user.

Figure 2A:
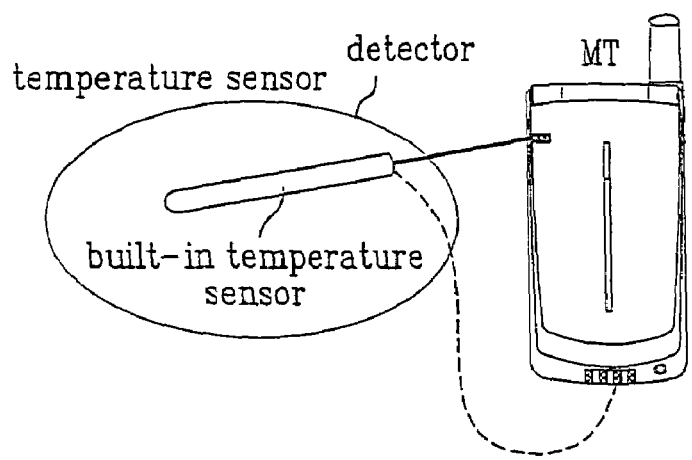
FIGS. 2A to 2C are views illustrating detectors used in the system according to the first embodiment of the present invention.
Figure 2B:
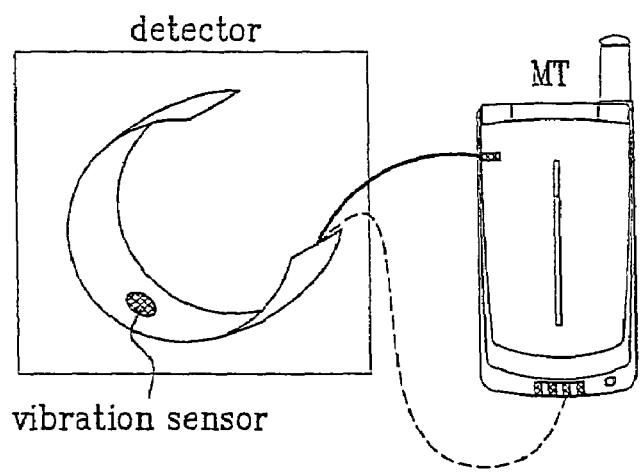
Figure 2C:
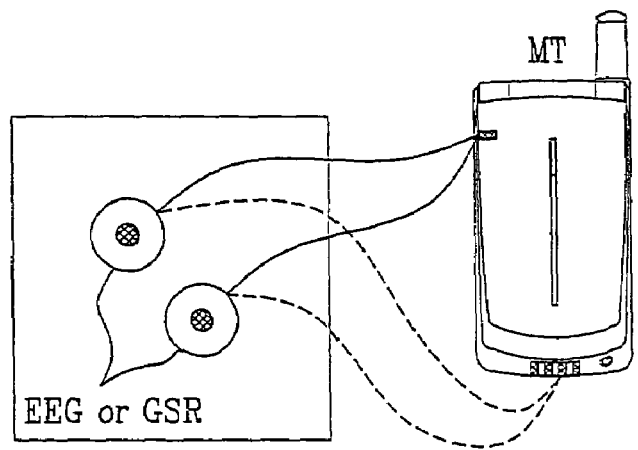

The detector 10 is shaped so as to easily perform a sensing operation as shown in FIGS. 2A to 2C.

The MT 20 repeats the user's body condition information sensed by the detector 10 to the server 40. At this time, the body condition information is repeated by wireless from the MT 20.

Also, the MT 10 instantly displays the body condition information simultaneously with the wireless repeat of the user's body condition information. This body condition information may be the body temperature, pulse, etc., that does not require a special medical diagnosis.

The MT 20 is also provided with a program 22 for controlling on/off and other operations of the detector 10, repeating by wireless sensed information transferred from the detector 10, and disclosing a result of health checkup transferred from the server 40. The program 22 discloses the health checkup result in the form of a text, sound, light, or image.

The MT 20 is also provided with at least one key for controlling on/off and other operations of the program 22. If the user presses the key, the MT 20 for the health checkup according to the present invention is driven.

The system according to the present invention further includes a connector 30 for electrically connecting the detector 10 to the MT 20.

Also, the MT 20 is provided with a signal input/output slot 21 composed of several metal faces. Here, through the first metal face are inputted/outputted a voice signal, a data signal, and a call control signal. The second metal face is electrically insulated from the first metal face, and receives input information of the sensors built in the detector 10.

The connector 30 has a jack to be inserted in the signal input/output slot 21. This jack is in contact with the second metal face.

Figure 3:
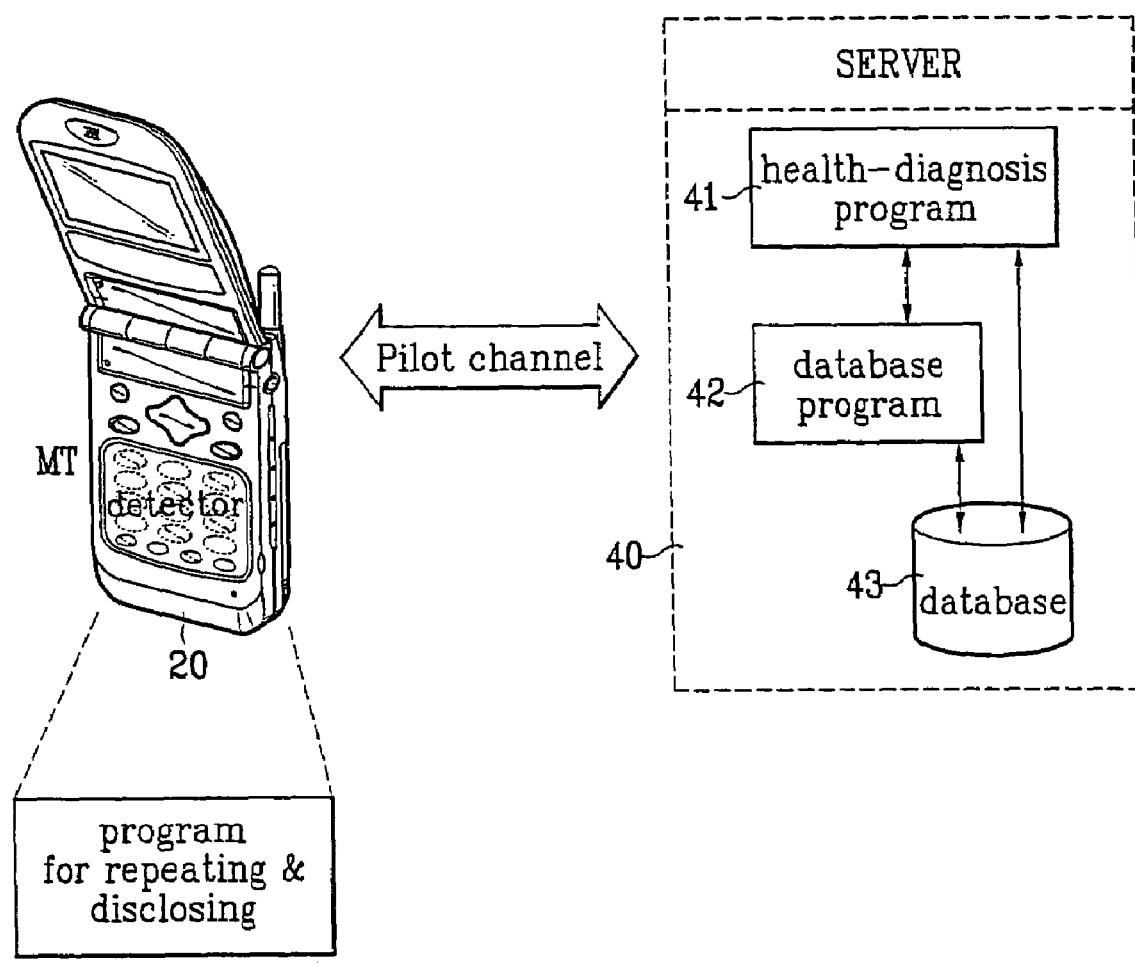
FIG. 3 is a view illustrating the construction of a system for performing a medical diagnosis in real time according to a second embodiment of the present invention.

FIG. 1 shows the system construction where the detector 10 is attached to the outside of the MT 20. As another example, FIG. 3 shows the system construction where the detector 10 is built in the MT 20. In case of the system of FIG. 3, the sensors of the detector 10 are attached to the surface of the MT 20 to detect the body condition information. The system of FIG. 3 provides better convenience in detecting the body temperature or pulse of the user.

The server 40 receives the body condition information of the user from the MT 20, analyzes the received condition information, and informs the result of health checkup to the MT 20.

For this, the server 40 is provided with a health-diagnosis program 41 for performing a health checkup based on the condition information received from the MT 20. The health-diagnosis program 41 repeats by wireless the result of diagnosis and the corresponding treatments to the MT 20. Accordingly, the program 22 built in the MT 20 discloses the diagnosis result and the corresponding treatments in the form of at least one of a text, sound, light, image, and combination thereof.

For instance, if the sensed value of the EEG sensor is transmitted to the server 40, the MT 20 receives from the server 40 and discloses music and/or light and/or image for improving the psychology of the user.

The server further includes a database 43 for storing information of the respective users such as the distinction of sex, age, weight, occupation, etc., and a database program 42 for inputting/outputting information to/from the database 43 through interworking with the provided health-diagnosis program 41. Here, the database program 42 also serves to update the information stored in the database 43. Specifically, the database program 43 updates and stores the present result of diagnosis performed by the health-diagnosis program 41 in the corresponding user area of the database 43, and in addition, stores the respective user's history of the diagnosis results performed by the health-diagnosis program 41 in the corresponding user area of the database 43.

The system according to the present invention does not affect the general call function of the MT 20 in a manner that the MT 20 repeats the sensed body condition information to the server 40 through a predefined reverse pilot channel, and on the contrary, the server informs the result of health checkup and the corresponding treatments through a predefined forward pilot channel.

Now, the system construction where the health-diagnosis capability of the server is excluded from the system illustrated in FIGS. 1 to 3 will be explained with reference to FIG. 4.

Figure 4:
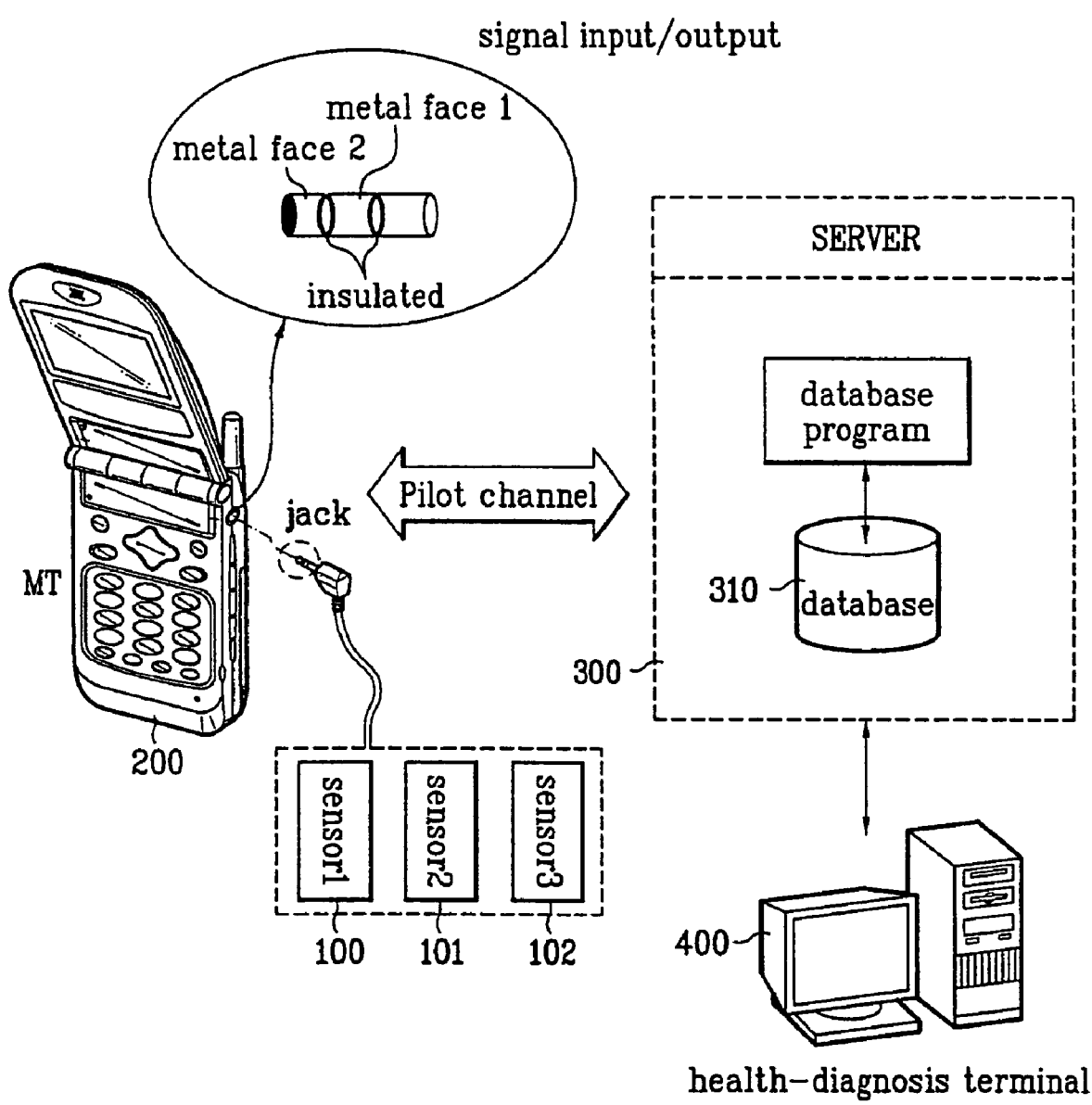
FIG. 4 is a view illustrating the construction of a system for performing a medical diagnosis in real time according to a third embodiment of the present invention.

FIG. 4 is a view illustrating the construction of a system for performing a medical diagnosis in real time according to a third embodiment of the present invention.

Referring to FIG. 4, the system includes sensors 100 to 102, an MT 200, a server 300, and a diagnosis terminal 400 for making a health checkup based on the user's body condition information sensed by the sensors 100 to 102.

The sensors 100 to 102 are for detection of temperature/vibration/conductive response and brain waves to sense the body condition of the user. For instance, the sensors may be a temperature sensor for sensing the body temperature of the user, a vibration sensor for sensing the pulse of the user, and a conductive response sensor for measuring a conductive response between specified regions of the user's body. Here, as the conductive response sensor is used a galvanic skin response (GSR) sensor. Also, the sensors may include an electroencephalogram (EEG) sensor for detecting the brain waves of the user. Especially, as the conductive response values between the specified body regions, bioelectric impedance values or frequency impedance values are detected.

The sensors 100 to 102 are shaped so as to easily perform the sensing operation as shown in FIGS. 2A to 2C.

The MT 202 repeats by wireless signals including the user's body condition information such as temperature values, vibration values, conductive response values, and brain wave values sensed by the sensors 100 to 102 and the user information of the MT 200 to the server 300.

The server 300 extracts the user information from the wireless repeated signal received from the MT 200, and performs a user authentication. If the user authentication is successful, the server 300 transmits the wireless repeated signal received from the MT 200 to a diagnosis terminal 400. Meanwhile, if the user authentication fails, the server 300 requests information required for the user authentication to the MT 200.

Then, the server 300 informs the MT 200 of the diagnosis result and/or the corresponding treatments received from the diagnosis terminal 400, and stores the received diagnosis result and/or the corresponding treatments in a storage area of a database 310 allocated to the user.

Especially, the server 300 informs the MT 200 of a pre-stored diagnosis history of the user along with the diagnosis result and/or the corresponding treatments currently received from the diagnosis terminal 400.

Then, the MT 200 displays the diagnosis result and/or the corresponding treatments, and the diagnosis history received from the server 300 by voice and/or text.

For instance, if the MT 200 transmits the brain wave value as the user's body condition information, the MT 200 receives from the server 300 and discloses music and/or light and/or image for improving the psychology of the user.

Next, the method of performing a health checkup in real time according to the present invention will be explained.

Figure 5:
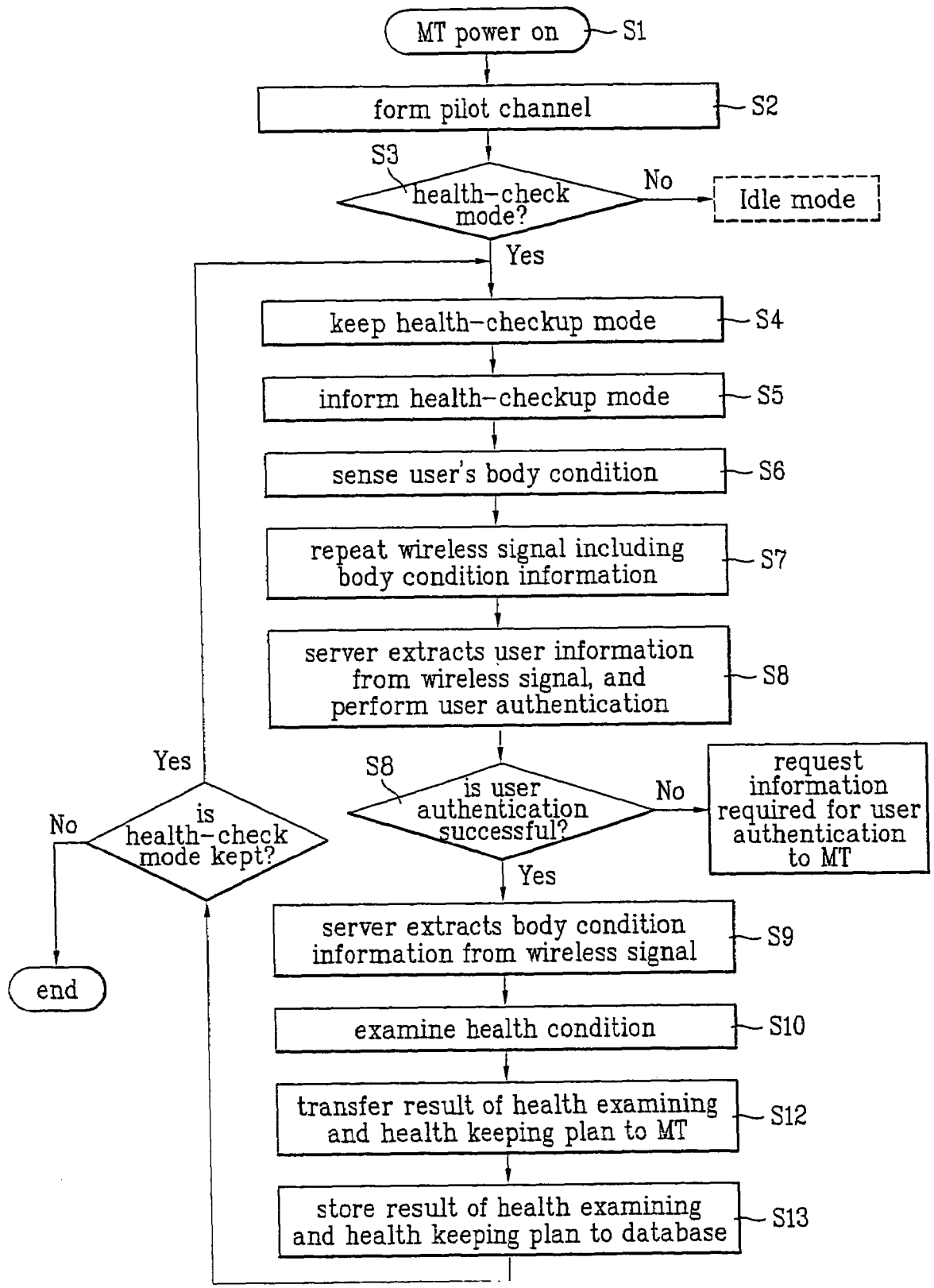
FIG. 5 is a flowchart illustrating a method of performing a medical diagnosis in real time according to the present invention.

FIG. 5 is a flowchart illustrating the method of performing a medical diagnosis in real time according to the present invention.

Referring to FIG. 5, the process of the health checkup in real time according to the present invention is performed on the basis of a wireless network system having an MT and a server.

If the power of the MT is on (step S1), a pilot channel is formed between the MT and the server (step S2).

Thereafter, if the user selects a health checkup mode by pressing a key provided in the MT (step S3), the MT keeps the health checkup mode (step S4). At this time, the state of the health checkup mode is displayed on the screen of the MT (step S5).

In the health checkup mode, the MT senses the body condition of the user (step S6). Specifically, through the sensors provided in the MT, the body temperature, pulse, conductive response value, and impedance value of electric response are detected as the body condition of the user. For instance, in a state that two terminals are grasped using both hands, respectively, the conductive response value and the impedance value between the two terminals, and the temperature and the pulse at the respective terminal are detected. Also, in a state that the two terminals are attached to two portions of the user's forehead, the brain waves are detected using the impedance value between the two terminals with the detection of temperature at the terminals. Also, in a state that one terminal is grasped by one hand and the other terminal is attached to a foot portion, or in a state that one terminal is attached to the chest, and the other terminal is attached to the back, the conductive response value or impedance value between the two terminals is detected.

Thereafter, the MT repeats the wireless signal including the sensed body condition to the server (step S7).

The server, after receiving the wireless signal, performs the user authentication by extracting the user information from the repeated wireless signal (step S8).

If the user authentication is successful, the server extracts the body condition information from the repeated wireless signal (step S9), and examines the health condition of the corresponding user using the extracted body condition information (step S10). Here, in case that the extracted information corresponds to the pulse, the health condition of the user is examined using the property and the condition of the pulse. Also, in case that the extracted information corresponds to the conductive response value, i.e., the impedance value of the electric response, for each body region, the nutritive condition, degree of fatness, and moisture distribution of the user's body are examined using the impedance value.

On the contrary, if the user authentication fails, the server requests the information required for the user authentication to the MT (step S11).

Then, the server transfers the result of health condition examination and the corresponding health keeping plan to the MT (step S12).

At the same time, the server stores the contents transferred to the MT, i.e., the result of health condition examination and the corresponding health keeping plan in the database (step S13).

Also, the server selectively provides the body condition information extracted from the wireless signal or the result of health condition examination to a medical institution or a protector. At this time, the medical institution may be a hospital predetermined by the user.

Now, an example of the above-described real-time health checkup process will be explained.

In a state that the power of the MT is on and in the health checkup mode, the MT detects the user's conductive response value of the MT user through the sensor having two terminals. In detail, the two terminals are attached to two portions of the user's forehead, and the conductive response value is detected from the impedance value of the electric response between the two terminals of the user's cranium.

Then, the MT repeats by wireless the detected conductive response value to the server.

The server analyzes the psychology of the user from the conductive response value repeated by wireless.

Then, the server transfers the corresponding treatments for improving the analyzed psychology to the MT. At this time, the server transfers the music and/or light and/or image for improving the analyzed psychology to the MT.

Next, another example of the above-described real-time health checkup process will be explained.

This health checkup process is performed on the basis of a wireless network system having an MT, server, and diagnosis terminal.

This case includes the same body condition sensing process and wireless repeating process as the procedure of FIG. 5.

Thereafter, the server performs the user authentication by extracting the user information from the repeated wireless signal.

If the user authentication is successful, the server transmits the wireless signal repeated from the MT to the diagnosis terminal. Here, the diagnosis terminal may be a terminal whose user is medical personnel, or a separate server having a program capable of performing a health checkup.

The diagnosis terminal examines the health condition by extracting the body condition information from the received wireless signal, and then transmits the result of examination and/or the corresponding treatments to the server.

Accordingly, the server transfers the result of examination and/or the corresponding treatments transmitted from the diagnosis terminal to the MT, and simultaneously stores them in its own database.

As described above, the system and method of performing the medical diagnosis in real time according to the present invention has the following effects.

First, the present invention enables the user to grasp his/her own health condition and feeling in real time through the MT that is always carried by the user, and thus helps the user to continuously check the health condition of the user.

Second, the present invention instantly informs the mobile terminal user of the actual health keeping plan and medical treatments based on the actual body information of the user, and the change of the health condition through interworking between the server existing in the wireless network or Internet and the MT, and thus enables the user to actively check his/her health condition any time and anywhere.

Third, the present invention transfers in real time the user's health checkup information processed by the server to the main hospital of the user, and thus provides the efficiency in health management.

It will be apparent to those skilled in the art than various modifications and variations can be made in the present invention. Thus, it is intended that the present invention covers the modifications and variations of this invention provided they come within the scope of the appended claims and their equivalents.

What is claimed is:

1. A mobile telephone comprising:
   a first sensor provided in the mobile telephone configured to sense a first body condition of a user of the mobile telephone;
   a receptacle for receiving a connector coupled to a second sensor for sensing a second body condition of the user; and
   a transmitter for transmitting the first and second body conditions sensed by the first sensor and the second sensor, wherein the receptable comprises:
   a first metal surface which inputs or outputs a voice signal, a data signal, or a call signal; and
   a second metal surface, insulated from the first metal surface, which receives a body condition signal from the second sensor.

2. The mobile telephone of claim 1, further comprising:
   a receiver to receive health information based upon the first and second body conditions sensed by the first sensor and the second sensor.

3. A mobile terminal, comprising:
   a receiver which receives voice information and health information from a mobile communications network; and
   a transmitter which transmits voice information and body sensor information to the mobile communications network, wherein the voice information is transmitted and received in association with a call and wherein the voice information, health information, and body sensor information are carried by different communication channels which include;
   a first control channel to carry the body sensor information from the transmitter to the mobile communications network,
   a second control channel to carry the health information from the mobile communications network to the receiver, and
   a voice channel to carry the voice information.

4. The mobile terminal of claim 3, wherein the health information is received in response to transmission of the body sensor information.

5. The mobile terminal of claim 4, wherein the health information includes a diagnosis result corresponding to the transmitted body sensor information.

6. The mobile terminal of claim 4, wherein the health information includes treatment information corresponding to the transmitted body sensor information.

7. The mobile terminal of claim 4, wherein the health information includes diagnosis history information received in response to the body sensor information.

8. The mobile terminal of claim 3, wherein the transmitter transmits user authentication information to authenticate the transmitted body sensor information.

9. The mobile terminal of claim 3, wherein the body sensor information is received from a sensor at least partially located within a terminal housing.

10. The mobile terminal of claim 3, wherein the body sensor information is received through an interface coupled to an external sensor.

11. The mobile terminal of claim 3, further comprising:
a memory storing a program which performs a control operation based on the health information received by the receiver.

12. The mobile terminal of claim 11, wherein the control operation includes outputting music from the terminal through a speaker.

13. The mobile terminal of claim 11, wherein the control operation includes outputting light from the terminal.

14. The mobile terminal of claim 11, wherein the control operation includes outputting an image on a display of the terminal.

15. The mobile terminal of claim 11, wherein the health information is received in response to transmission of the body sensor information, and wherein the control operation includes outputting at least one external stimulus to achieve a predetermined psychology of a terminal user.

16. The mobile terminal of claim 15, wherein the at least one external stimulus is selected from the group consisting of sound, light, and an image.

17. The mobile terminal of claim 3, further comprising:
an interface which selectively carries first and second signals, wherein the first signal includes a voice signal, a data signal, or a call signal and the second signal includes the body sensor information.

18. The mobile terminal of claim 3, wherein the first control channel carries the body sensor information and the second control channel carries the health information independent from call functions performed by the terminal.

19. The mobile terminal of claim 3, wherein the first control channel carries the body sensor information and the second control channel carries the health information while the voice channel carries voice signals corresponding to a general call that is unrelated to a health condition of a user of the mobile terminal.

20. The mobile terminal of claim 3, further comprising:
an output device; and
a controller that controls a function of the output device based on the health information received through the second control channel.

21. The mobile terminal of claim 20, wherein the controller controls display of a text message selected to affect a psychology of a user of the mobile terminal in a way that matches a diagnosis included in the received health information.

22. The mobile terminal of claim 20, wherein the controller controls display of an image selected to affect a psychology of a user of the mobile terminal in a way that matches a diagnosis included in the received health information.

23. The mobile terminal of claim 20, wherein the controller controls output of a sound selected to affect a psychology of a user of the mobile terminal in a way that matches a diagnosis included in the received health information.

24. The mobile terminal of claim 20, wherein the controller controls a light function of the terminal in a way that produces a desired affect on a psychology of a user that matches a diagnosis included in the received health information.

25. A mobile terminal comprising:
a receiver which receives voice information and health information from a mobile communications network;
a transmitter which transmits voice information and body sensor information to the mobile communications network, wherein the voice information is transmitted and received in association with a call and wherein the voice information, health information, and body sensor information are carried by different communication channels; and
an interface which selectively carries first and second signals, wherein the first signal includes a voice signal, a data signal, or a call signal and the second signal includes the body sensor information, wherein the interface includes a receptacle having:
a first metal surface which conveys the first signal, and
a second metal surface which is insulated from the first metal surface and receives the second signal from a sensor.

26. The mobile terminal of claim 25, wherein the first and second metal surfaces are spaced by a predetermined amount to provide said insulation.

27. A mobile telephone comprising:
an alphanumeric keypad to enter digits corresponding to a telephone number;
a display unit to display the telephone number;
a memory that stores a control program to receive information from one or more body sensors;
means for sending body control information received from the one or more sensors on a first control channel; and
means for receiving health information on a second control channel.

28. The mobile telephone of claim 27, further comprising:
means for sending voice information over a voice channel.

* * * * *